(12) United States Patent
Kishimoto

(10) Patent No.: US 6,723,065 B2
(45) Date of Patent: Apr. 20, 2004

(54) INTRAOCULAR SURGICAL APPARATUS

(76) Inventor: Makoto Kishimoto, 1-10-8, Moriyama, Moriyama-shi, Shiga-ken (JP)

(*) Notice: Subject to any disclaimer, the term of this patent is extended or adjusted under 35 U.S.C. 154(b) by 81 days.

(21) Appl. No.: 09/741,031

(22) Filed: Dec. 21, 2000

(65) Prior Publication Data

US 2002/0095113 A1 Jul. 18, 2002

(30) Foreign Application Priority Data

Dec. 22, 1999 (JP) .......................... 11-364413

(51) Int. Cl.$^7$ .................. A61M 3/00; A61M 31/00; A61M 1/00; A61F 9/00
(52) U.S. Cl. ............... 604/43; 604/27; 604/35; 604/45; 604/48; 606/107; 606/166
(58) Field of Search ............... 604/67, 23, 43, 604/156, 122, 118, 27–48; 600/398, 561, 500; 606/107, 166; 417/540; 137/206–209

(56) References Cited

U.S. PATENT DOCUMENTS

| 4,841,984 A | 6/1989 | Armeniades et al. |
| 5,476,448 A | 12/1995 | Urich |
| 5,766,146 A | * 6/1998 | Barwick, Jr. .................. 604/28 |
| 5,979,494 A | * 11/1999 | Perkins et al. ............... 137/102 |
| 6,283,937 B1 | 9/2001 | Takamatsu et al. |

FOREIGN PATENT DOCUMENTS

| EP | 0180317 | 5/1976 |
| EP | 0862902 A3 | 9/1998 |
| EP | 0862902 A2 | 9/1998 |
| JP | 01207059 | 8/1989 |
| JP | 07-000442 | 1/1995 |
| JP | 10-43229 | 2/1998 |
| JP | 2002-153499 | 11/2000 |

OTHER PUBLICATIONS

BUI, Constant Ocular Pressure Active Infustion system, Fed. 14, 2002, U.S. patent application Publication, PUB No. US 2002/0019607 A1.*

* cited by examiner

*Primary Examiner*—Michael J. Hayes
*Assistant Examiner*—Roz Ghafoorian
(74) *Attorney, Agent, or Firm*—Crowell & Moring LLP

(57) ABSTRACT

An intraocular surgical apparatus including an introduction tube for introducing perfusate into a closed intraocular affected part, a discharge tube for discharging the affected part and the perfusate, a perfusate feed passage connected to the introduction tube and incorporating a perfusate reservoir for feeding the perfusate with a predetermined rest liquid head pressure, a valve for controlling the amount of perfusate fed from the reservoir to the introduction tube, and a discharge passage connected to the discharge tube and incorporating a suction pump. The perfusate feed passage further incorporates, at a passage portion thereof from the control valve to an outlet opening of the introduction tube, a pressure-reduction compensating means for feeding supplementary perfusate into the closed intraocular affected part through a supplementing passage having a smaller passage resistance than the perfusate feed passage in the event of and in association with abnormal pressure reduction inside the affected part.

15 Claims, 5 Drawing Sheets

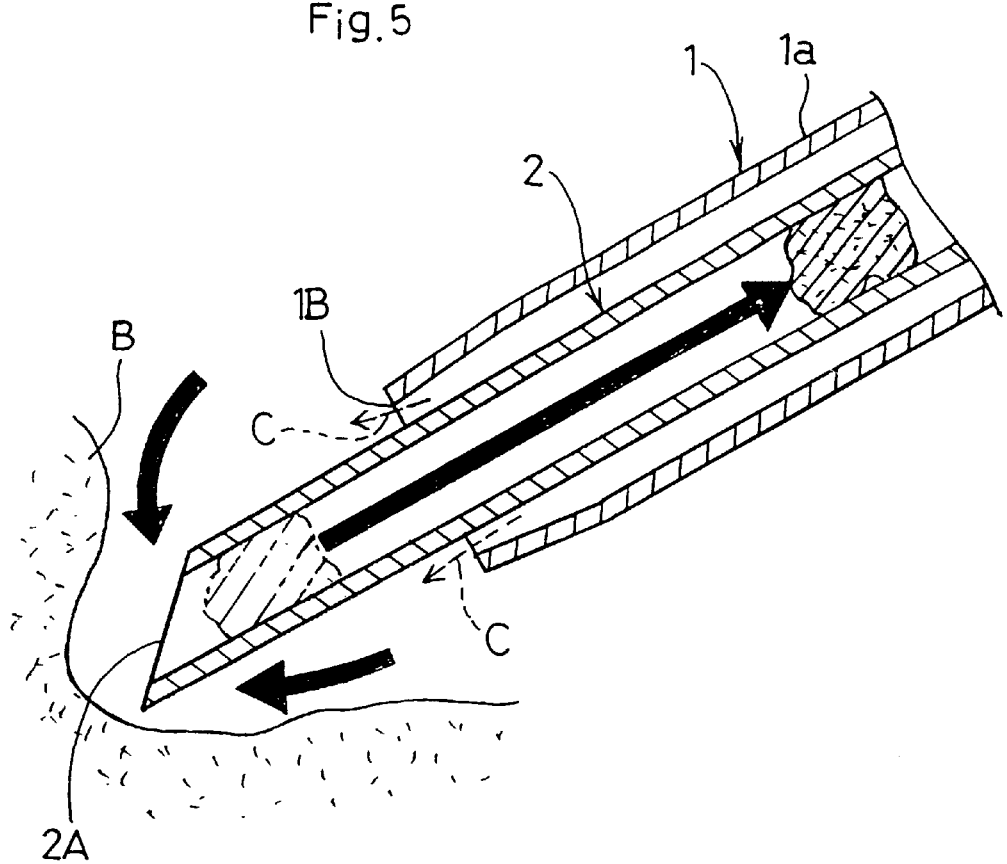

INTRAOCULAR SURGICAL APPARATUS

BACKGROUND OF THE INVENTION

This application claims the priority of JP 11-364413, file Dec. 22, 1999, the disclosure of which is expressly incorporated by reference herein.

1. Field of the Invention

The present invention relates to an intraocular surgical apparatus for use in a surgical operation for treating, e.g., cataract.

2. Description of the Related Art

In recent years, for treatment of eye diseases such as cataract, a surgical operation is often carried out to replace the affected crystalline lens in the eye of the subject with an intraocular lens (artificial crystalline lens). In this respect, as an operation for extirpating such an affected part as the crystalline lens, there is known the ultrasonic emulsifying aspirating operation (KPE) for applying ultrasonic waves to the affected part, e.g., crystalline lens, for pulverizing (emulsifying) the part and simultaneously aspirating and discharging the pulverized part to the outside.

A typical apparatus for use in such an ultrasonic emulsifying aspirating operation is shown in FIG. 4. The apparatus includes a handpiece 3 having an introduction tube 1 for introducing perfusate (artificial aqueous humor) C into the closed intraocular affected part B and a discharge tube 2 for discharging the emulsified affected part together with the perfusate C. A perfusate feed passage D connected to the introduction tube 1 incorporates a perfusate reservoir E capable of feeding the perfusate C with a predetermined rest liquid head pressure (h). A discharge passage G connected to the discharge tube 2 of the handpiece 3 incorporates a suction pump H for controlling the operation of a switch valve F of the feed passage D to open the valve F in association with an aspirating operation or to close it in association with stopping of the aspirating operation.

When operating an apparatus constructed as described above, an outlet opening 1B of the introduction tube 1 and an aspiration opening 2A of the discharge tube 2 of the handpiece 3 are inserted together into the closed intraocular affected part B through a small access incision made in the cornea or sclera of the eye to be treated.

Then, ultrasonic waves are applied to the affected part, such as a crystalline lens, for gradual emulsification. At the same time the emulsified part is aspirated and discharged to the outside by the suction force of the suction pump H. During this step, the switch valve F incorporated in the perfusate feed passage D is opened in response to the operation of the suction pump H. Open switch valve F allows the introduction, in association with the sucking action of the pump, of fresh perfusate C into the intraocular affected part B via the introduction tube 1. The amount of fresh perfusate C introduced into the intraocular affected part B corresponds to the amount of material aspirated and discharged from the perfusate reservoir E. This balances the flow rate of perfusate and the suction force of the suction pump.

However, as illustrated in FIG. 5, it sometimes happens that the introduced part may be momentarily stuck at the aspiration opening 2A of the discharge tube 2 and then suddenly released therefrom to be drawn toward the discharging side. In the case of such an excessive aspiration phenomenon, because the perfusate feed passage D provides certain passage resistance and the outflow rate of the perfusate C from the outlet opening 1B of the introduction tube 1 is fixedly governed by the effect of free-fall, the balance between the inflow amount from the introduction tube 1 and the outflow or discharge amount from the discharge tube 2 is lost, with the latter exceeding the former. This leads to momentary abnormal pressure reduction and development of negative pressure within the closed intraocular affected part B compared with a normal pressure in the case of a normal operation. The negative pressure may result in a so-called micro-collapse phenomenon characterized by reduction in the content volume of the eyeball and the anterior chamber. In an extreme case, such a micro-collapse phenomenon may result in rupture of the posterior capsule or damage in the endothelium camerae anterioris.

Customarily, when a surgeon notices the possibility of such a phenomenon, the surgeon will expediently adjust the amount of ultrasonic waves and/or the aspiration amount in such a manner as to avoid it. However, in order for the surgeon to be able to do so, they need a good amount of practice with animal or artificial eyes for training as well as a considerable amount of actual experience in the surgery.

SUMMARY OF THE INVENTION

The present invention pertains to the above-described state of the art. The primary object of the invention is to provide an improved intraocular surgical apparatus which effectively prevents occurrence of the micro-collapse phenomenon in the eyeball and the anterior chamber in the event of abnormal pressure reduction in the closed intraocular affected part due to momentary clogging of the affected part at, e.g., the inlet opening of the discharge tube and subsequent sudden movement thereof toward the discharging side.

For fulfilling the above-noted object, according to one aspect of the present invention, an intraocular surgical apparatus is provided, comprising:

an introduction tube for introducing perfusate into a closed intraocular affected part;

a discharge tube for discharging the affected part together with the perfusate;

a perfusate feed passage connected to the introduction tube, the perfusate feed passage incorporating a perfusate reservoir capable of feeding the perfusate with a predetermined rest liquid head pressure, and a control valve for controlling the amount of perfusate to be fed from the perfusate reservoir to the introduction tube; and a discharge passage connected to the discharge tube, the discharge passage incorporating a suction pump;

wherein the perfusate feed passage further incorporates, at a passage portion thereof from the control valve to an outlet opening of the introduction tube, a pressure-reduction compensating means capable of feeding a supplementary amount of perfusate into the closed intraocular affected part through a supplementing passage having a smaller passage resistance than the perfusate feed passage in the event of and in association with abnormal pressure reduction inside the affected part.

With the above-described construction, in the event of abnormal pressure reduction in the closed intraocular affected part due to momentary clogging of the affected part (at, e.g., the inlet opening of the discharge tube) and subsequent sudden release and movement thereof toward the discharging side, in operative association with this pressure reduction, the pressure-reduction compensating means can supply, through the supplementing passage, a supplementary amount of perfusate to the affected part in order to compensate for the pressure reduction. Accordingly, occurrence of micro-collapse in the eyeball and the anterior chamber can be effectively prevented, so that the surgical operation may take place in a safe and reliable manner.

In the above construction, the pressure-reduction compensating means is provided midway to the perfusate feed passage. Since the passage resistance becomes smaller closer to the inlet opening of the discharge tube, it is preferred that the pressure-reduction compensating means be provided at a position near the inlet opening of the discharge tube. It is also to be noted that the control valve incorporated within the perfusate feed passage can be a variable-flow control valve instead of a switch valve.

According to one preferred embodiment of the present invention, the pressure-reduction compensating means includes a supplementary perfusate reservoir storing a portion of the perfusate flowing within the perfusate feed passage and acting as a supplementing passage, and a gas reservoir for reserving gas compressed under the predetermined rest liquid head pressure of the perfusate reservoir. With this construction, in the event of abnormal pressure reduction in the closed intraocular affected part due to momentary clogging of the affected part (at, e.g., the inlet opening of the discharge tube) and subsequent sudden release and movement thereof toward the discharging side, in association with this reduction, expansion of the gas reserved in the gas reservoir under the compressed state occurs, which expansion causes an immediate reverse flow of the perfusate portion in the supplementing perfusate reservoir, as the supplementing passage of the pressure-reduction compensating means has a smaller passage resistance than the perfusate feed passage, into the intraocular affected part. Therefore, the construction with this additional feature can prevent occurrence of-the micro-collapse phenomenon in the eyeball and the anterior chamber more reliably and can ensure an even more reliable and safer surgical operation.

According to a further preferred embodiment of the invention, the introduction tube and the discharge tube are provided in a handpiece which includes an ultrasonic-wave-generating means capable of applying ultrasonic waves focused in the vicinity of the inlet opening of the discharge tube. With this feature, the affected part is emulsified with the ultrasonic waves and this emulsified part is discharged together with the perfusate, in the event of abnormal pressure reduction in the closed intraocular affected part due to momentary clogging of the affected part (at, e.g., the inlet opening of the discharge tube) and subsequent sudden release and movement thereof toward the discharging side. Then, in association with or triggered by this pressure reduction, expansion of the gas reserved in the gas reservoir under the compressed state occurs, which expansion causes immediate reverse flow of the perfusate portion in the supplementing perfusate reservoir, because the supplementing passage of the pressure-reduction compensating means has a smaller passage resistance than the perfusate feed passage, into the intraocular affected part. Therefore, construction with this additional feature can prevent occurrence of micro-collapse in the eyeball and the anterior chamber more reliably. Hence, this construction can be employed in, e.g., the ultrasonic emulsifying aspirating operation (KPE) for significantly improving its safety and reliability.

According to a further embodiment of the invention, the supplementary perfusate reservoir and the gas reservoir of the pressure-reduction compensating means are constructed in the form of a single flexible continuous tube. This construction can improve the maneuverability of the apparatus so as to not interfere with the surgical operation and can improve also the handling of the apparatus. Moreover, the construction facilitates attachment of the pressure-reduction compensating means to an existing system such as a system used for the ultrasonic emulsifying aspirating operation. This attachment requires only a minor modification of the system, such as use of a connector, e.g., a branch-joint tube, capable of connecting the tube to the inlet opening of the introduction tube of the handpiece. The readiness of the attachment will contribute to widespread use of the apparatus of the invention.

According to a further embodiment of the invention, the flexible tube constituting the supplementary perfusate reservoir and the gas reservoir of the pressure-reduction compensating means is made of silicone.

Silicone material has the advantage of high resistance against chemical influence. Silicone is advantageous also in that it can be reused after, e.g., sterilization. Moreover, if the silicone is translucent, then the translucence provides visibility from the outside of the supplementary perfusate reservoir and the gas reservoir disposed inside, thus facilitating preparation for a surgical operation. Further, if a mark is provided between the supplementary perfusate reservoir and the gas reservoir, this will help accuracy in the preparation, thus further improving the handling of the apparatus.

According to a further embodiment of the invention, the tube constituting the supplementary perfusate reservoir and the gas reservoir of the pressure-reduction compensating means is provided at an upper end of the gas reservoir, and is opened and closed by an opening-closing means. With this feature, the leading end of the tube constituting the pressure-reduction compensating means is raised and then closed by the opening-closing means. Then, a switch valve incorporated in the perfusate feed passage is opened to allow introduction of the perfusate from the perfusate reservoir into the tube with the predetermined rest liquid head pressure applied to this feed passage, thereby forming the supplementary perfusate reservoir. At the upper portion of the supplementary perfusate reservoir, the gas reservoir may then be formed for reserving gas compressed under the predetermined rest liquid head pressure of the perfusate reservoir via the supplementary perfusate present in the supplementary perfusate reservoir. That is, the supplementary perfusate reservoir and the gas reservoir of the pressure-reduction compensating means may be readily formed by using an ordinary tube. Moreover, the preparation of the pressure-reduction compensating means may be performed quickly.

According to a further embodiment of the invention, the tube constituting the supplementary perfusate reservoir and the gas reservoir of the pressure-reduction compensating means is detachably connected and in communication with the perfusate feed passage connected to the introduction tube. With this feature, the detachability of the tube facilitates the assembly and disassembly of the apparatus for storage after use. The detachability also facilitates sterilization and replacement of the apparatus or its parts when needed. Furthermore, by detaching the tube and then attaching a plug instead, any other conventional surgical operation can be effected. In this manner, different intraocular surgical apparatuses may be used interchangeably, depending on the need.

According to a further embodiment of the invention, the tube constituting the supplementary perfusate reservoir and the gas reservoir of the pressure-reduction compensating means has an inner diameter substantially equal to that of a tube constituting the perfusate feed passage. With this feature, advantages may be obtained. If one of the tubes has a different diameter from the diameter of the other tube, the perfusate will flow from the large-diameter tube into the small-diameter tube, hence providing a resistance at the transition region. By using tubes with equal diameters, such resistance does not occur and the apparatus can cope with the pressure variation, i.e., reduction from the normal pressure at the time of normal operation, in the closed intraocular affected part, in a more reliable and speedy manner.

According to a further embodiment of the invention, the gas reservoir of the pressure-reduction compensating means is charged with inert gas. With this feature, the supplementing perfusate reservoir is placed in contact with a non-reactive gas atmosphere, allowing sterilization. This further adds to the reliability and the safety of the surgical operation.

According to an embodiment of the pressure-reduction compensating means of the intraocular surgical apparatus relating to the present invention, the pressure-reduction compensating means, when provided at a passage portion of the perfusate feed passage from the control valve to an outlet opening of the introduction tube, is capable of feeding a supplementary amount of perfusate into the closed intraocular affected part through a supplementing passage having a smaller passage resistance than the perfusate feed passage in the event of and in association with abnormal pressure reduction inside the affected part. With this feature, when the pressure-reduction compensating means is provided midway to the perfusate feed passage, in the event of abnormal pressure reduction in the closed intraocular affected part due to momentary clogging of the affected part (at, e.g., the inlet opening of the discharge tube) and subsequent sudden release and movement thereof toward the discharging side, in association with this reduction, the pressure-reduction compensating means is capable of feeding a supplementary amount of perfusate into the closed intraocular affected part through a supplementing passage having a smaller passage resistance than the perfusate feed passage. Therefore, the construction can prevent occurrence of the micro-collapse phenomenon in the eyeball and the anterior chamber.

According to an embodiment of the tube constituting the pressure-reduction compensating means set forth in the present invention, a branch-joint tube is provided for branch-connecting a base end of the tube to the perfusate feed passage as a member for forming the supplementary perfusate reservoir and the gas reservoir of the pressure-reduction compensating means inside the tube as being connected and in communication with the perfusate feed passage. With this feature, in the attachment of the pressure-reduction compensating means to an existing system, such as a system used for the ultrasonic emulsifying aspirating operation, because the branch-joint tube is provided in advance as being connected to the base end of the tube constituting the pressure-reduction compensating means, this attachment can be done easily by connecting this branch-joint tube to the inlet opening of the introduction tube of the handpiece. This readiness of the attachment will contribute to widespread use of the apparatus of the invention.

According to a further embodiment of the tube constituting the pressure-reduction compensating means of the present invention, an opening-closing means for opening and closing the leading end of the tube formed at the upper end of the gas reservoir is provided as a member for forming the supplementary perfusate reservoir and the gas reservoir of the pressure-reduction compensating means inside the tube as being connected and in communication with the perfusate feed passage. With this feature, the leading end of the tube constituting the pressure-reduction compensating means is raised and then closed by the opening-closing means. Then, a switch valve incorporated in the perfusate feed passage is opened to allow introduction of the perfusate from the perfusate reservoir into the tube with the predetermined rest liquid head pressure applied to this feed passage to form the supplementary perfusate reservoir. At the upper portion of this supplementary perfusate reservoir, the gas reservoir may then be formed for reserving gas compressed under the predetermined rest liquid head pressure of the perfusate reservoir via the supplementary perfusate present in this supplementary perfusate reservoir. That is, the supplementary perfusate reservoir and the gas reservoir of the pressure-reduction compensating means may be readily formed by using such very simple construction. The preparation of the pressure-reduction compensating means may be performed quickly.

According to a further embodiment of the tube constituting the pressure-reduction compensating means of the present invention, to form the supplementary perfusate reservoir and the gas reservoir of the pressure-reduction compensating means inside the tube being connected and in communication with the perfusate passage, a branch-joint tube is provided. The branch-joint tube branch-connects a base end of the tube to the perfusate feed passage. An opening-closing means for opening and closing the leading end of the tube formed at the upper end of the gas reservoir is provided. With this feature, the tube constituting the pressure-reduction compensating means as being connected and in communication with the perfusate feed passage is raised with its leading end oriented upward. Then, the leading end of this tube is closed by the opening-closing means and a switch valve incorporated in the perfusate feed passage is opened to allow introduction of the perfusate from the perfusate reservoir into the tube with the predetermined rest liquid head pressure applied to this feed passage to form the supplementary perfusate reservoir. At the upper portion of this supplementary perfusate reservoir, the gas reservoir may then be formed for reserving gas compressed under the predetermined rest liquid head pressure of the perfusate reservoir via the supplementary perfusate present in this supplementary perfusate reservoir. That is, the supplementary perfusate reservoir and the gas reservoir of the pressure-reduction compensating means may be readily formed by using such very simple construction. The preparation of the pressure-reduction compensating means may be performed quickly. Furthermore, in the attachment of the pressure-reduction compensating means to an existing system such as a system used for the ultrasonic emulsifying aspirating operation, as the branch-joint tube is provided in advance as being connected to the base end of the tube constituting the pressure-reduction compensating means, this attachment can be done easily by connecting this branch-joint tube to the inlet opening of the introduction tube of the handpiece. This readiness of the attachment will contribute to widespread use of the apparatus of the invention.

Further and other objects, features and advantages of the invention will become apparent from the following detailed description of the preferred embodiments with reference to the accompanying drawings.

BRIEF DESCRIPTION OF THE DRAWINGS

FIG. 5 is an enlarged section showing conditions of principal portions of the conventional apparatus.

DESCRIPTION OF THE PREFERRED EMBODIMENTS

Figure 1:
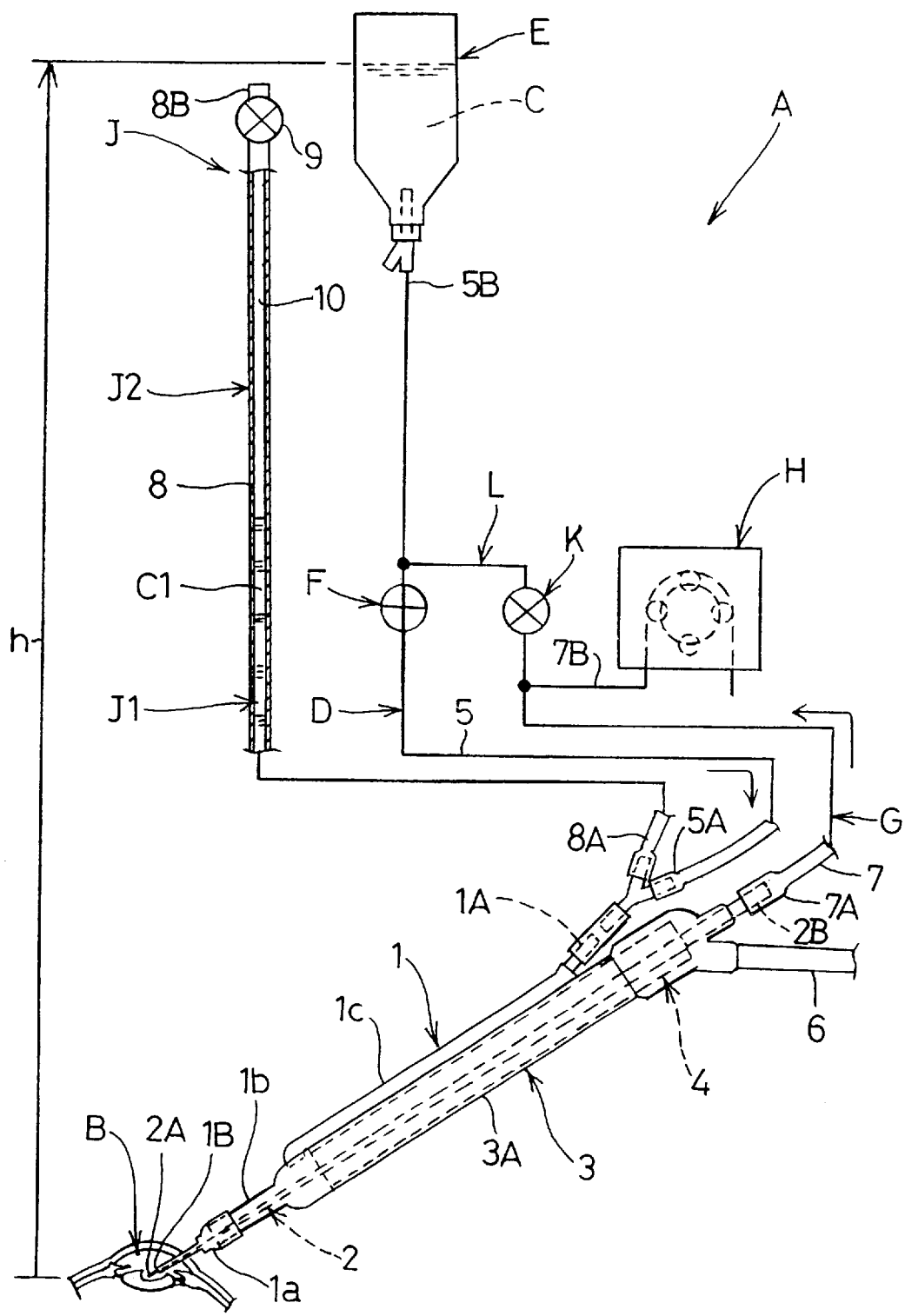
FIG. 1 is a view showing an intraocular surgical apparatus according to one preferred embodiment of the present invention for illustrating its operational principle.
Figure 2:
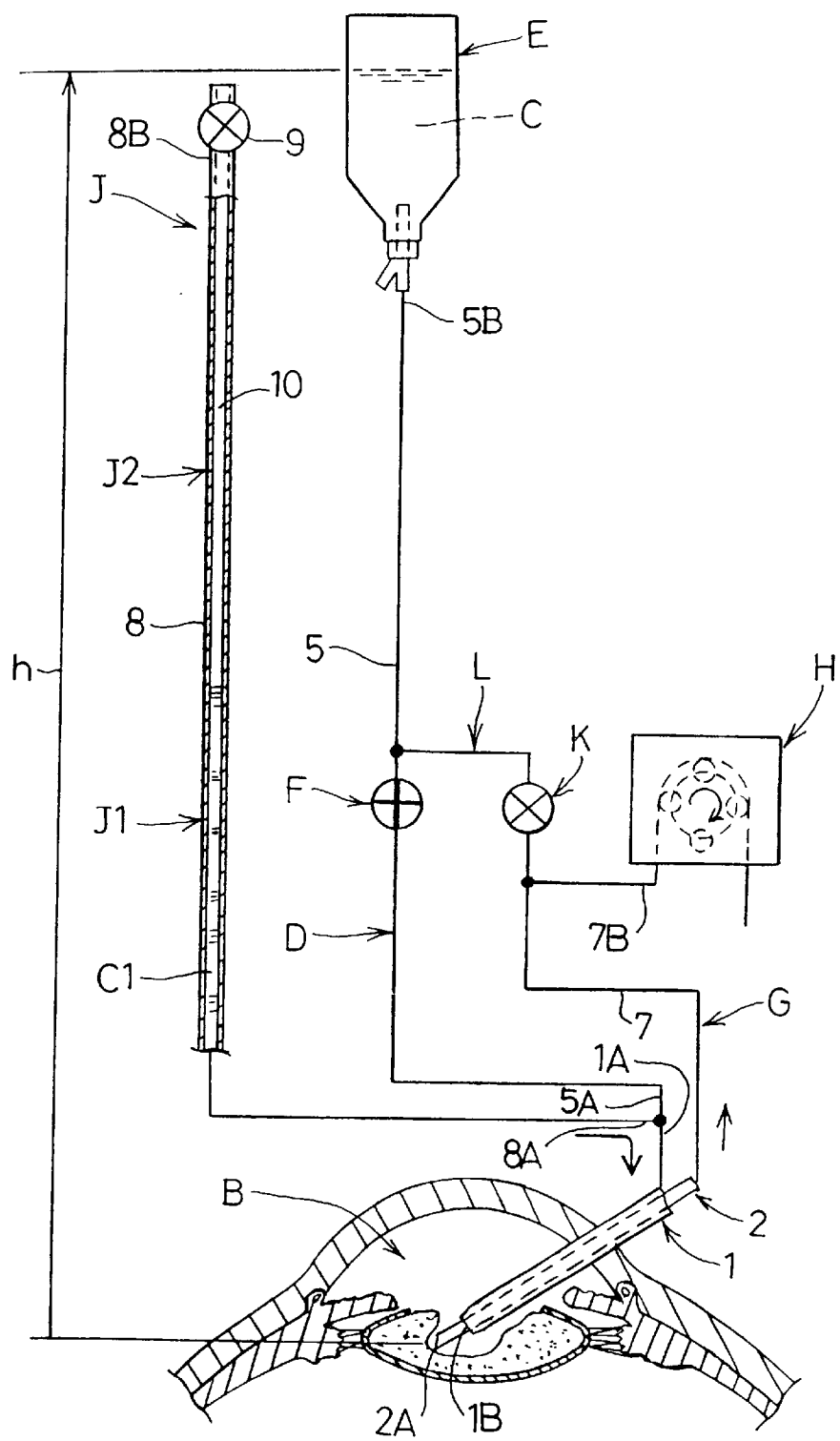
FIG. 2 is a view showing principal portions of the intraocular surgical apparatus for also illustrating its operational principle.
Figure 3:
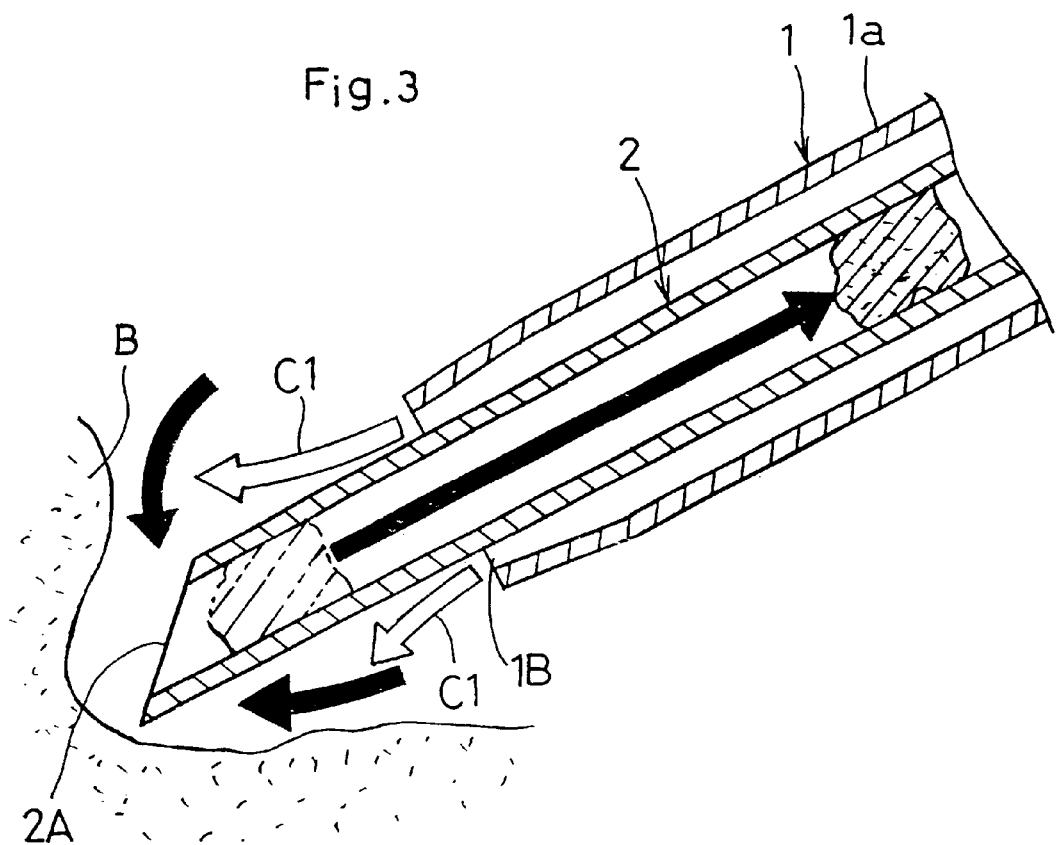
FIG. 3 is an enlarged section showing conditions of the principal portions of the intraocular surgical apparatus.
Figure 4:
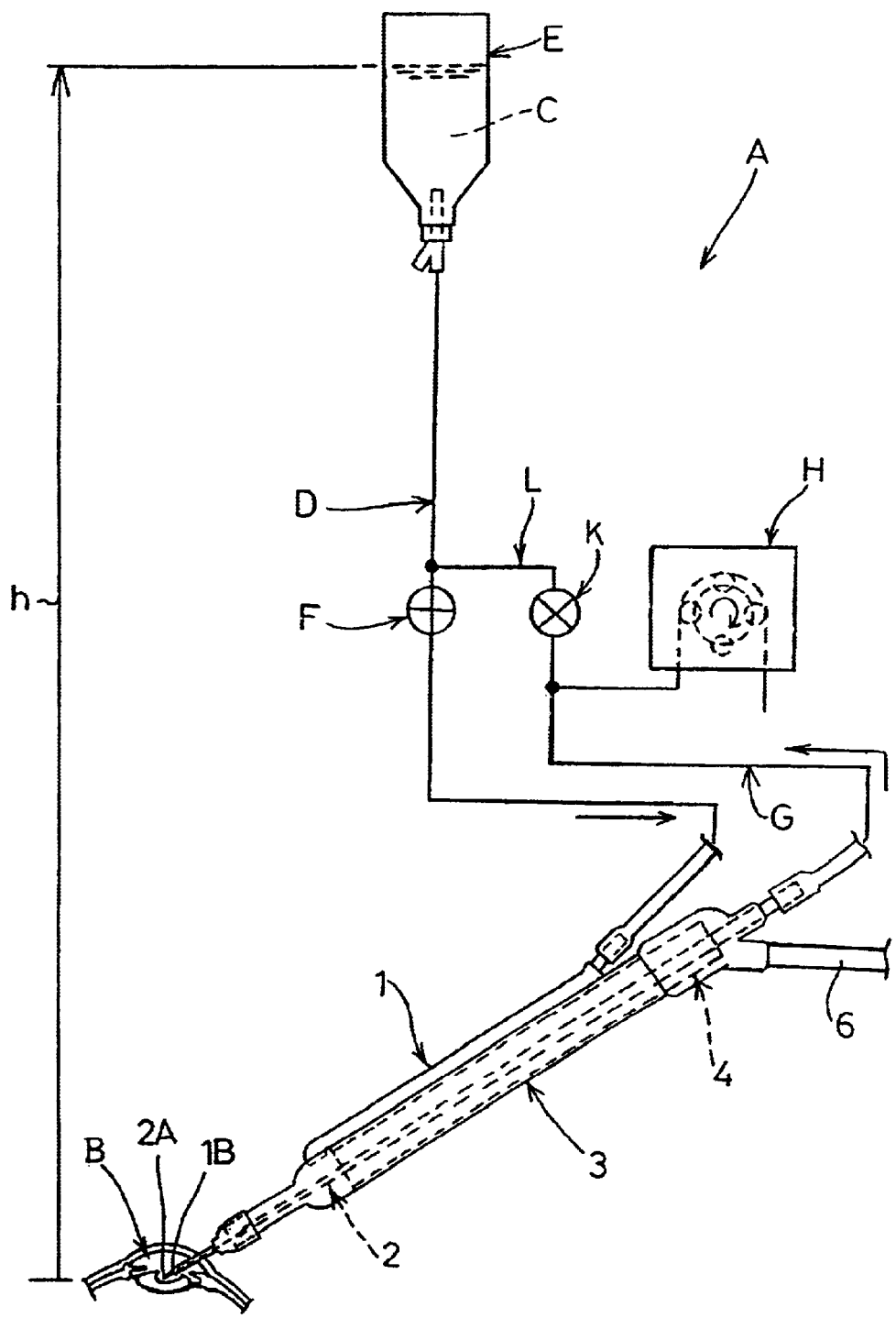
FIG. 4 is a view showing the intraocular surgical apparatus according to the prior art for illustrating its operational principle.

FIGS. 1–3 show an intraocular surgical apparatus according to one preferred embodiment of the present invention.

As shown in FIG. 1, apparatus A includes a handpiece 3 having an introduction tube 1 for introducing perfusate (artificial aqueous humor) C into the closed intraocular affected part B and a discharge tube 2 for discharging the affected part together with the perfusate C. A perfusate feed passage D connected to the introduction tube 1 incorporates a perfusate reservoir E capable of feeding the perfusate C with a predetermined rest liquid head pressure (h). A discharge passage G connected to the discharge tube 2 of the handpiece 3 incorporates a suction pump H for controlling operation of a switch valve F of the feed passage D to open the valve F in association with an aspirating operation or to close the valve F when stopping the aspirating operation. The apparatus further includes a pressure-reduction compensating means J consisting essentially of a supplementary perfusate reservoir J1 storing a portion C1 of the perfusate C flowing within the perfusate feed passage and acting as a supplementing passage, and a gas reservoir J2 for reserving gas 10 compressed under a predetermined rest liquid head pressure (h) of the perfusate reservoir E. In operation, the pressure-reduction compensating means J is capable of feeding a supplementary amount of perfusate C1 from the supplementary perfusate reservoir J1 to the inside of a closed intraocular affected part through the supplementing passage having a smaller passage resistance than that of the perfusate feed passage D in the event of and in association with occurrence of abnormal pressure reduction inside the affected part.

The introduction tube 1 includes a perfusate tip 1a forming an outlet opening 1B at the leading end of a grip portion 3A of the handpiece 3, a receiver tube portion 1b for detachably receiving the perfusate tip 1a, and a junction tube portion 1c in communication with the receiver tube portion 1b and formed continuously along a lateral face of the grip portion 3A of the handpiece 3. Further, the introduction tube 1 defines, at the rear end thereof, an inlet opening 1A connectable with the perfusate feed passage D for communication therewith.

The discharge tube 2, in the form of a capillary coaxial with the perfusate tip 1a of the introduction tube 1, is disposed inside through the handpiece 3, such that an aspiration opening 2A defined at the leading end thereof is disposed at a position slightly projecting from the outlet opening 1B of the perfusate tip 1a, and a connecting outlet 2B defined at the rear end thereof is disposed at a position projecting from the rear end of the handpiece 3 to be connectable with the discharge passage G for establishing communication therewith.

The aspiration opening 2A at the leading end of the discharge tube 2 constitutes an "aspirating port".

The specific shapes and/or configurations of the perfusate tip 1a of the introduction tube 1 and the aspirating port of the discharge tube 2 can vary in many ways, depending on the aspiration procedure, type of surgical operation, location of use, object of the aspiration discharge, preference of the surgeon, and other factors. For instance, the outlet opening 1B of the perfusate tip 1a can be formed in a direction normal to the introducing direction into the discharge tube 2. Further, the cutoff angle of the aspiration opening 2A of the discharge tube 2 for acting as the aspirating port can be varied in many ways.

The grip portion 3A of the handpiece 3 accommodates therein a device such as an oscillating device, a focusing device, etc. These devices are connected via a cable 6 with a circuitry (not shown) including an output control unit, a power unit, and optional other units disposed outside, so that the devices together constitute an ultrasonic wave generating means 4. This ultrasonic wave generating means 4 is constructed so that ultrasonic waves therefrom are focused at the axial position of the aspiration opening 2A of the discharge tube 2.

The perfusate feed passage D is formed by a flexible tube 5 made of silicone. A base end portion 5A of this tube 5 is connected to and in communication with the inlet opening 1A of the introduction tube 1. Further, a leading end 5B of the tube 5 is connected and in communication with the perfusate reservoir E which is filled with the perfusate C and disposed at a position of a predetermined adjustable altitude from a predetermined maneuvering position of the handpiece 3, so that with establishment of connection/communication between the perfusate reservoir E and the leading end 5B of the tube 5, the perfusate C can be fed to the introduction tube 1 with a predetermined rest liquid head pressure (h).

The altitude of the perfusate reservoir E is adjustable from approximately 65 cm to 75 cm away from the location of the intraocular affected part B of the patient to be treated.

The perfusate reservoir E is provided in the form of a single glass or vial which is filled with the perfusate C prepared by diluting a predetermined drug solution with diluent. Specifically, this perfusate C can be the commercially available "BSS-PLUSTM™" which is a preparation made by diluting oxyglutathione solution with diluent according to a predetermined dilution ratio.

Further, the switch valve F incorporated within the flexible tube 5 constituting the perfusate feed passage D comprises, e.g., a pinch valve which is a control valve capable of controlling the flow rate of the perfusate C depending on whether the valve F is fully opened or closed. A control scheme is provided for closing this switch valve F of the perfusate feed passage D in response to and in operative association with the sucking operation of the suction pump H and the closing of valve F in response to cessation of the suction operation by the suction pump H. This control scheme is based on detection by a pressure sensor provided within the discharge passage G or detection of an ON/OFF state of a pump driving motor for driving the suction pump H. In addition to the pinch valve, the switch valve F may alternatively comprise an electromagnetic type switch valve, a spring-loaded switch valve, or other device.

The discharge passage G is formed by a flexible tube 7 made of silicone. A base end portion 7A of this tube 7 is connected to and in communication with the outlet opening 2B of the discharge tube 2. A leading end 7B of the tube 7 is connected with the suction pump H so as to allow suction in the discharge tube 2.

The suction pump H can be a peristaltic pump, venturi pump, diaphragm pump, or other device. Pumps differ in some respects, e.g., rising speed up to a predetermined suction pressure. Among the pump options, a peristaltic pump is particularly preferred, which is capable of rising its suction pressure from a basic suction pressure and allows individual or independent settings of the suction pressure and the flow rate. With this type of suction pump, the suction pressure can be increased or decreased in a controllable manner by increasing or decreasing the rotational speed of the pump driving motor for driving it.

In the case of the peristaltic pump, the suction amount is about 0–44 cc/min, and the suction pressure about 0–500 mm Hg. The outer diameter of the outlet opening 1B formed at the leading end of the introduction tube 1 is about 1 mm, and the outer diameter of the aspiration opening 2A of the discharge tube 2 is about 0.3 mm.

Adjustments of the oscillation or generation amount of the ultrasonic waves by the ultrasonic wave generating means 4 and the suction pressure of the suction pump H, can be made by means of a foot switch (not shown) operable to activate and cause the generating means or the pump to be shifted from an initial value to a predetermined higher value upon an operator's stepping the foot switch. The pump is deactivated upon release of the user's foot therefrom. Alternatively, it can be operated in a continuously variable, i.e., proportional, manner depending on the "step-on depth" or amount of the stepping-on operation.

The pressure-reduction compensating means J is formed mainly of a flexible tube 8 of silicone. Its base end 8A is branch-connected via a branch-joint tube to the inlet opening 1A of the introduction tube 1, and its leading end 8B is closed by being clamped by a clamp 9 acting as opening/closing means. Hence, within tube 8, there are formed the supplementary perfusate reservoir J1 storing a portion C1 of the perfusate C and the gas reservoir J2 for reserving gas compressed under the predetermined rest liquid head pressure (h) of the perfusate reservoir E. The supplementary perfusate reservoir J1 is formed by the introduction of tube 1 in communication with a portion of the tube 8 other than the gas reservoir J2. The perfusate portion reserved within this reservoir is referred to as the supplementary perfusate C1.

The leading end 8B of the tube 8 is disposed above the maneuvering area of the handpiece 3 and also below the set height of the perfusate reservoir E so as to ensure the formation of the supplementary perfusate reservoir J1 and the gas reservoir J2 inside the tube 8.

Further, for closing the leading end 8B of the tube 8, instead of the clamp 9 described above, a manual operation type switch valve can be attached. Alternatively, a plug may be detachably attached.

In this embodiment, the tube 5 forming the perfusate feed passage D, the tube .7 forming the discharge passage G, and the tube 8 forming the pressure-reduction compensating means J have an equal inner diameter.

Between the perfusate feed passage D and the discharge passage G, there is connected a bypass passage L incorporating a bypass switch valve K.

When needed, by opening the bypass switch valve K, closing the switch valve F of the perfusate feed passage D, and deactivating the suction pump H, reverse flow of the perfusate C is allowed from the aspiration opening 2A of the discharge tube 2. Further, depending on necessity, by opening the bypass switch valve K, closing the switch valve F, then activating the suction pump H, any perfusate C remaining in the perfusate reservoir E may be forcibly discharged.

With the above-described construction in operation, first, in the initial empty condition of the tube 8 with both the switch valve F of the perfusate feed passage D and the bypass switch valve K closed, the leading end of this empty tube 8 will be closed by the opening/closing means 9. Next, the switch valve F of the perfusate feed passage D is opened to allow the perfusate C to be released from the inlet opening 1A of the introduction tube 1 at the predetermined rest liquid head pressure (h). Under this condition, the leading end of the handpiece 3 will be sealingly closed with a plug (not shown), so that the inlet opening 1A of the introduction tube 1 and the aspiration opening 2A of the discharge tube 2 will be accommodated within the closed space filled with the perfusate C.

In this condition, with the introduction of the perfusate via the tube 5 into the tube 8, there are formed within the latter, the supplementary perfusate reservoir J1 and the gas reservoir J2 upwardly thereof for reserving gas 10 compressed under the effect of the predetermined rest liquid head pressure (h) of the perfusate reservoir E. The portion of the tube 5 extending from the perfusate reservoir E and accommodating the perfusate C therein forms the perfusate feed passage D.

Subsequently, for example by test-operating the suction pump H, the perfusion condition of the perfusate C within the closed circuit will be confirmed. This completes the preparatory procedure of the apparatus.

Upon completion of the preparation of the intraocular surgical apparatus A described above, the closing plug will be removed from the leading end of the handpiece 3, and the inlet opening 1a of the introduction tube 1 of the handpiece 3 and the aspiration opening 2A of the discharge tube 2 will be inserted into the closed intraocular affected part B through a small incision made in the cornea.

Then, as illustrated in FIG. 2, ultrasonic waves will be applied to the affected part, such as the crystalline lens, for gradually emulsifying it. At the same time the emulsified part will be aspirated and discharged to the outside under the suction force from the suction pump H. Concomitantly, the switch valve F incorporated within the perfusate feed passage D will be opened in response to the activation of the suction pump H, so that an amount of new perfusate C corresponding to the amount used and discharged will be fed into the introduction tube 1 into the intraocular affected part B, thus balancing the perfusion amount and the suction pressure with each other. In this normal condition, there is no problem of passage resistance, so that the supplementary perfusate reservoir J1 and the gas reservoir J2 of the pressure-reduction compensating means J are being maintained under equilibrium so as to hold the supplementary perfusate C1 retained within the tube 8 portion forming the supplementary perfusate reservoir J1. Accordingly, in this condition, the perfusate C will be perfused from the perfusate reservoir E into the intraocular affected part B.

As illustrated in FIG. 3, in the event of abnormal pressure reduction in the closed intraocular affected part due to momentary clogging of the affected part at, e.g., the aspiration opening 2A of the discharge tube 2 and subsequent sudden release and movement thereof toward the discharging side, in response to and in operative association with this phenomenon, the compressed gas 10 reserved within the gas reservoir J2 will be expanded, thereby causing the supplementary perfusate C1 present within the supplementary perfusate reservoir J1 to flow immediately in reverse from reservoir J1 into the intraocular affected part B, whereby the balance between the perfusate rate and the suction pressure of the suction pump H may be maintained.

In the embodiment described above, the handpiece 3 includes the ultrasonic wave generating means 4. However, in the case of treatment of cataract, if its core is not too hard (i.e., a hardness of about Grade 1), the cataract may be aspirated and discharged without using ultrasonic waves. Therefore, the present invention may be applied to an intraocular surgical apparatus not having or not using any ultrasonic wave generating means 4.

A further embodiment relates to an intraocular surgical apparatus adapted for aspirating and discharging the affected portion directly from the closed intraocular affected part, without relying on the ultrasonic wave generating means 4 described and employed in the foregoing embodiment.

In a previously described embodiment, the gas reservoir J2 of the pressure-reduction compensating means J is charged with gas 10. In an alternative embodiment, this gas reservoir J2 of the pressure-reduction compensating means J can be charged with inert gas.

In a previously described embodiment, the pressure-reduction compensating means J includes the supplementary perfusate reservoir J1 for reserving the perfusate portion C1 and the gas reservoir J2 both formed within the tube 8 so as to be balanced with the predetermined rest liquid pressure (h) of the perfusate reservoir E. In an alternative embodiment, the pressure-reduction compensating means J can consist of the supplementary perfusate reservoir J1 formed within the tube 8 and a gas reservoir J2 also formed within the tube 8 in the form of a spherical dome.

Also, the pressure-reduction compensating means J may comprise a combination of the supplementary perfusate reservoir J1 and a diaphragm connected with supplementary perfusate reservoir J1.

In the foregoing embodiment, the switch valve F incorporated in the perfusate feed passage D is an ON/OFF-type switch valve F which controls the flow rate of the perfusate depending on whether it is fully opened or fully closed. Instead, this valve can be a flow-control valve capable of variably and continuously controlling the flow rate of the perfusate C.

In the foregoing embodiment, the perfusate reservoir E is provided in the form of a single glass bottle or vial filled with the perfusate C prepared by dilution of an appropriate drug solution with diluent, with the perfusate reservoir E being connected to the perfusate feed passage D. The present invention is not limited to this construction. Alternatively, a plurality of perfusate reservoirs E may be provided to be disposed at different altitudes from each other, with one of these reservoirs E being selectively connectable to the perfusate feed passage D via a switch valve associated therewith.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. An intraocular surgical apparatus comprising:

an introduction tube for introducing perfusate into a closed intraocular affected part;

a discharge tube for discharging the affected part together with the perfusate;

a perfusate feed passage connected to the introduction tube, the perfusate feed passage incorporating a perfusate reservoir capable of feeding the perfusate with a predetermined rest liquid head pressure and a control valve for controlling the amount of the perfusate to be fed from the perfusate reservoir to the introduction tube;

a discharge passage connected to the discharge tube, the discharge passage incorporating a suction pump;

wherein the perfusate feed passage further incorporates, at a passage portion thereof from the control valve to an outlet opening of the introduction tube, a pressure-reduction compensating means capable of feeding a supplementary amount of the perfusate into the closed intraocular affected part through a supplementing passage having a smaller passage resistance than the perfusate feed passage in the event of and in association with abnormal pressure reduction inside the affected part;

wherein the pressure-reduction compensating means includes a supplementary perfusate reservoir storing a portion of the perfusate flowing within the perfusate feed passage and acting as the supplementing passage and a gas reservoir for reserving gas compressed under the predetermined rest liquid head pressure of the perfusate reservoir; and wherein the supplementary perfusate reservoir and the gas reservoir of the pressure-reduction compensating means are constructed in the form of a single flexible continuous tube.

2. The apparatus according to claim 1, wherein the introduction tube and the discharge tube are provided in a handpiece which includes and ultrasonic-wave generating means capable of applying ultrasonic waves in focus onto vicinity of the inlet opening of the discharge tube.

3. The apparatus according to claim 1, wherein the flexible tube constituting the supplementary perfusate reservoir and the gas reservoir of the pressure-reduction compensating means is made of silicone.

4. The apparatus according to claim 1, wherein the tube constituting the supplementary perfusate reservoir and the gas reservoir of the pressure-reduction compensating means is provided at an upper end of the gas reservoir to be opened and closed by opening-closing means.

5. The apparatus according to claim 1, wherein the tube constituting the supplementary perfusate reservoir and the gas reservoir of the pressure-reduction compensating means is detachably connected and communicated with the perfusate feed passage connected to the introduction tube.

6. The apparatus according to claim 1, wherein the tube constituting the supplementary perfusate reservoir and the gas reservoir of the pressure-reduction compensating means has an inner diameter substantially equal to that of the tube constituting the perfusate feed passage.

7. The apparatus according to claim 1, wherein the gas reservoir of the pressure-reduction compensating means is charged with inert gas.

8. A tube constituting the pressure-reduction compensating means for use in the intraocular surgical apparatus of claim 1, comprising a branch-joint tube for branch-connecting a base end of the tube to the perfusate feed passage.

9. A tube constituting the pressure-reduction compensating means for use in the intraocular surgical apparatus of claim 1, comprising an opening-closing means for opening and closing a leading end of the tube formed at an upper end of the gas reservoir.

10. A tube constituting the pressure-reduction compensating means for use in the intraocular surgical apparatus of claim 1, comprising:

a branch-joint tube for branch-connecting a base end of the tube to the perfusate feed passage; and an opening-closing means for opening and closing a leading end of the tube formed at an upper end of an gas reservoir.

11. A pressure-reduction compensating means for use in an intraocular surgical apparatus including an introduction tube for introducing perfusate into a closed intraocular affected part and a discharge tube for discharging the affected part together with the perfusate, comprising:

a supplementary perfusate reservoir storing a portion of the perfusate; and a gas reservoir for reserving gas compressed under a pressure of the perfusate present inside the introduction tube, wherein the supplementary perfusate reservoir and the gas reservoir of the pressure-reduction compensating means are constructed in the form of a single flexible continuous tube; and wherein the pressure-reduction compensating means is capable of feeding a supplementary amount of the perfusate into the closed intraocular affected part through the introduction tube in the event of and in association with abnormal pressure reduction inside the affected part.

12. The pressure-reduction compensating means of claim 11, further comprising branch-joint tube for branch-connecting a base end of the continuous tube to the introduction tube.

13. The pressure-reduction compensating means of claim 11, wherein a passage resistance between the pressure-reduction compensating means and the introduction tube is set smaller than a passage resistance of the introduction tube.

14. The pressure-reduction compensating means of claim 11, further comprising opening-closing means for opening and closing the leading end of the tube formed at the upper end of the gas reservoir.

15. The pressure-reduction compensating means of claim 11, further comprising:

a branch-joint tube for branch-connecting a base end of the continuous tube to the introduction tube; and an opening-closing means for opening and closing the leading end of the tube formed at the upper end of the gas reservoir.

* * * * *